(12) United States Patent
Sverrisson et al.

(10) Patent No.: US 9,387,096 B2
(45) Date of Patent: Jul. 12, 2016

(54) FEEDBACK CONTROL SYSTEMS AND METHODS FOR PROSTHETIC OR ORTHOTIC DEVICES

(75) Inventors: Ragnar Sverrisson, Reykjavik (IS); Arinbjörn V. Clausen, Reykjavik (IS)

(73) Assignee: Ossur HF, Reykjavik (IS)

( * ) Notice: Subject to any disclaimer, the term of this patent is extended or adjusted under 35 U.S.C. 154(b) by 865 days.

(21) Appl. No.: 12/816,968

(22) Filed: Jun. 16, 2010

(65) Prior Publication Data

US 2010/0324698 A1 Dec. 23, 2010

Related U.S. Application Data

(60) Provisional application No. 61/187,955, filed on Jun. 17, 2009.

(51) Int. Cl.
*A61F 2/68* (2006.01)
*A61F 2/58* (2006.01)
*A61B 5/103* (2006.01)
*A61B 5/00* (2006.01)
(Continued)

(52) U.S. Cl.
CPC ............... *A61F 2/58* (2013.01); *A61B 5/1038* (2013.01); *A61B 5/4528* (2013.01); *A61F 2/60* (2013.01); *A61F 2/64* (2013.01); *A61F 2/68* (2013.01); *A61F 2002/704* (2013.01); *A61F 2002/705* (2013.01); *A61F 2002/7615* (2013.01)

(58) Field of Classification Search
CPC ............... A61F 2/60; A61F 2/64; A61F 2/68; A61F 2/6607; A61F 2002/704

USPC .......................................................... 623/24
See application file for complete search history.

(56) References Cited

U.S. PATENT DOCUMENTS 3,820,168 A 6/1974 Horvath
3,866,246 A 2/1975 Seamone et al.
(Continued)

FOREIGN PATENT DOCUMENTS

DE 4229330 3/1994
EP 1531767 12/2008
(Continued)

OTHER PUBLICATIONS

PCT International Search Report and Written Opinion, PCT/US2010/033788, dated Jul. 6, 2010.
(Continued)

*Primary Examiner* — Bruce E Snow
*Assistant Examiner* — Melissa Hoban
(74) *Attorney, Agent, or Firm* — Knobbe, Martens, Olson & Bear LLP (57) ABSTRACT

Methods and systems are used for monitoring a global position or location of a prosthetic or orthotic device and to provide feedback control of the device. Certain methods may employ remote transmitting devices and receivers to recognize when a prosthetic or orthotic device user is in a moving vehicle and, therefore, initiate automatic shut-off, driving mode, or relaxed mode. Other methods may employ remote transmitting devices and receivers to identify the global position of the prosthetic or orthotic device, compare the global position to a stored terrain mapped database and output feedback control instructions and/or alerts to the prosthetic or orthotic device based at least in part on the stored terrain mapping information.

15 Claims, 5 Drawing Sheets

(51) Int. Cl.
  *A61F 2/60* (2006.01)
  *A61F 2/64* (2006.01)
  *A61F 2/70* (2006.01)
  *A61F 2/76* (2006.01)

(56) References Cited

U.S. PATENT DOCUMENTS

| | | |
|---|---|---|
| 3,995,324 A | 12/1976 | Burch |
| 4,209,860 A | 7/1980 | Graupe |
| 4,314,379 A | 2/1982 | Tanie |
| 4,808,187 A | 2/1989 | Patterson et al. |
| 4,876,944 A | 10/1989 | Wilson et al. |
| 4,878,913 A | 11/1989 | Aebischer et al. |
| 5,062,857 A | 11/1991 | Berringer |
| 5,252,102 A | 10/1993 | Singer et al. |
| 5,253,656 A | 10/1993 | Rincoe et al. |
| 5,336,269 A | 8/1994 | Smits |
| 5,376,128 A | 12/1994 | Bozeman |
| 5,383,939 A | 1/1995 | James |
| 5,413,611 A | 5/1995 | Haslam et al. |
| 5,443,524 A | 8/1995 | Sawamura et al. |
| 5,458,655 A | 10/1995 | Bozeman |
| 5,480,454 A | 1/1996 | Bozeman |
| 5,571,205 A | 11/1996 | James |
| 5,695,527 A | 12/1997 | Allen |
| 5,888,212 A | 3/1999 | Petrofsky et al. |
| 5,888,213 A | 3/1999 | Sears et al. |
| 5,893,891 A | 4/1999 | Zahedi |
| 5,953,683 A | 9/1999 | Hansen et al. |
| 6,113,642 A | 9/2000 | Petrofsky et al. |
| 6,122,960 A * | 9/2000 | Hutchings et al. .............. 73/493 |
| 6,423,098 B1 | 7/2002 | Biedermann |
| 6,443,993 B1 | 9/2002 | Koniuk |
| 6,517,585 B1 | 2/2003 | Zahedi et al. |
| 6,522,266 B1 | 2/2003 | Soehren et al. |
| 6,610,101 B2 | 8/2003 | Herr et al. |
| 6,645,252 B2 | 11/2003 | Asai et al. |
| 6,679,920 B2 | 1/2004 | Biedermann et al. |
| 6,695,885 B2 | 2/2004 | Schulman et al. |
| 6,719,806 B1 | 4/2004 | Zahedi et al. |
| 6,740,123 B2 | 5/2004 | Davalli et al. |
| 6,755,870 B1 | 6/2004 | Biedermann et al. |
| 6,764,520 B2 | 7/2004 | Deffenbaugh et al. |
| 6,875,241 B2 | 4/2005 | Christesen |
| 7,131,998 B2 | 11/2006 | Pasolini |
| 7,147,667 B2 | 12/2006 | Bédard |
| 7,198,071 B2 | 4/2007 | Bisbee, III et al. |
| 7,279,009 B2 | 10/2007 | Herr et al. |
| 7,314,490 B2 | 1/2008 | Bédard et al. |
| 7,431,737 B2 | 10/2008 | Ragnarsdottir et al. |
| 7,455,696 B2 | 11/2008 | Bisbee, III et al. |
| 7,531,006 B2 | 5/2009 | Clausen et al. |
| 7,578,799 B2 * | 8/2009 | Thorsteinsson et al. .......... 602/5 |
| 7,602,301 B1 * | 10/2009 | Stirling et al. ............. 340/573.1 |
| 7,637,959 B2 | 12/2009 | Clausen et al. |
| 7,691,154 B2 | 4/2010 | Asgeirsson et al. |
| 7,736,394 B2 | 6/2010 | Bédard et al. |
| 7,794,505 B2 | 9/2010 | Clausen et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bedard et al. |
| 7,867,284 B2 | 1/2011 | Bedard |
| 7,896,927 B2 | 3/2011 | Clausen et al. |
| 7,953,549 B2 * | 5/2011 | Graham et al. ............... 701/466 |
| 7,955,398 B2 | 6/2011 | Bedard et al. |
| 8,025,632 B2 | 9/2011 | Einarsson |
| 8,048,172 B2 | 11/2011 | Jonsson et al. |
| 8,057,550 B2 | 11/2011 | Clausen et al. |
| 2004/0054423 A1 | 3/2004 | Martin |
| 2004/0064195 A1 | 4/2004 | Herr |
| 2004/0064286 A1 | 4/2004 | Levi et al. |
| 2005/0234562 A1 | 10/2005 | Okuda et al. |
| 2005/0283257 A1 | 12/2005 | Bisbee et al. |
| 2006/0135883 A1 * | 6/2006 | Jonsson ....................... 600/546 |
| 2006/0136072 A1 | 6/2006 | Bisbee et al. |
| 2006/0173552 A1 | 8/2006 | Roy |
| 2006/0184252 A1 | 8/2006 | Oddsson et al. |
| 2006/0184280 A1 | 8/2006 | Oddsson et al. |
| 2006/0206215 A1 | 9/2006 | Clausen et al. |
| 2006/0249315 A1 * | 11/2006 | Herr et al. ...................... 180/8.1 |
| 2007/0050047 A1 | 3/2007 | Ragnarsdottlr et al. |
| 2007/0270722 A1 | 11/2007 | Loeb et al. |
| 2009/0024062 A1 | 1/2009 | Einarsson |
| 2009/0024065 A1 | 1/2009 | Einarsson |
| 2009/0054996 A1 * | 2/2009 | Sykes et al. ..................... 623/24 |
| 2009/0056445 A1 * | 3/2009 | Veltink ...................... 73/514.01 |
| 2009/0171469 A1 * | 7/2009 | Thorsteinsson et al. ......... 623/26 |
| 2009/0265018 A1 * | 10/2009 | Goldfarb et al. ............... 623/40 |
| 2009/0299063 A1 | 12/2009 | Gilbert et al. |
| 2009/0312844 A1 * | 12/2009 | Ikeuchi et al. ................... 623/40 |
| 2010/0113980 A1 * | 5/2010 | Herr et al. ..................... 600/587 |
| 2010/0114329 A1 * | 5/2010 | Casler et al. ..................... 623/24 |
| 2010/0185124 A1 | 7/2010 | Bisbee et al. |
| 2010/0286796 A1 | 11/2010 | Clausen |
| 2010/0324456 A1 | 12/2010 | Jónsson et al. |
| 2010/0324698 A1 | 12/2010 | Sverrisson et al. |
| 2011/0106274 A1 | 5/2011 | Ragnarsdottir et al. |
| 2011/0125290 A1 | 5/2011 | Langlois |
| 2011/0224804 A1 | 9/2011 | Clausen et al. |
| 2011/0245931 A1 | 10/2011 | Clausen et al. |
| 2011/0264230 A1 * | 10/2011 | Herr et al. .................. 623/22.11 |
| 2012/0016492 A1 | 1/2012 | Clausen |

FOREIGN PATENT DOCUMENTS

| | | |
|---|---|---|
| GB | 2201260 | 8/1988 |
| WO | WO 99/08621 | 2/1999 |

OTHER PUBLICATIONS

PCT International Search Report and Written Opinion, dated Sep. 1, 2010, PCT Application PCT/US2010/038886.

* cited by examiner

FEEDBACK CONTROL SYSTEMS AND METHODS FOR PROSTHETIC OR ORTHOTIC DEVICES

RELATED APPLICATION

This application claims the benefit of U.S. Provisional Application No. 61/187,955, filed Jun. 17, 2009, the entirety of which is hereby incorporated by reference to be considered part of this specification.

BACKGROUND

1. Field

Embodiments of the invention relate to controlling prosthetic or orthotic devices and, in particular, to positioning sensing systems and methods for controlling such devices.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

The number of disabled persons and amputees is increasing each year as the average age of individuals increases, as does the prevalence of debilitating diseases such as diabetes. As a result, the need for prosthetic and orthotic devices is also increasing. Conventional orthoses are often used to support a joint, such as an ankle or a knee, of an individual, and movement of the orthosis is generally based solely on the energy expenditure of the user. Some conventional prostheses are equipped with basic controllers that artificially mobilize the joints without any interaction from the amputee and are capable of generating only basic motions. Such basic controllers do not take into consideration the dynamic conditions of the working environment. The passive nature of these conventional prosthetic and orthotic devices typically leads to movement instability, high energy expenditure on the part of the disabled person or amputee, gait deviations and other short- and long-term negative effects. This is especially true for leg orthoses and prostheses.

SUMMARY

While the technology for orthotic and prosthetic devices has advanced to include basic sensor systems capable of providing some degree of feedback control to the controllers, these sensors have mainly included proximity sensors, load sensors, accelerometers, tactile sensors, and/or pressure sensors that are coupled to the device. Thus, basic controllers still mainly act based on information about the micro-environment, or the environment directly surrounding the device user. For example, a prosthetic or orthotic device user may be situated in a moving vehicle, such as a car, train, or plane. With only a basic sensor system, the prosthetic or orthotic device may not recognize that the device user is changing positions at a rate of about 30 miles per hour and may only respond to the immediate environment, such as a pressure or load on the limb. In certain situations, this lack of crucial information may lead to dangerous movements of the prosthetic device or orthotic assisted limb. Therefore, there is still the need for sensors that would provide prosthetic and orthotic device users with additional information regarding movement of the device and/or its user.

In certain embodiments of the invention, feedback control systems and methods for motion-controlled prosthetic and orthotic devices are provided. These systems and methods include utilizing a sensor, in communication with a remote transmitting source, to detect when an actively-adjustable prosthetic or orthotic system is located in or on a moving vehicle. In certain embodiments, the sensor includes a global positioning system sensor or receiver. For instance, if the global positioning system, operatively coupled with other sensors on the prosthetic or orthotic system, detects that the prosthetic or orthotic user is seated in a moving vehicle, the prosthetic or orthotic system may initiate automatic shut-off.

In certain embodiments, the remote transmitting source also measures directionality and/or movement of the actively adjustable prosthetic or orthotic system. In certain embodiments, the sensor information can then be compared with defined gait patterns. If the sensor information corresponds to known unsafe gait patterns, the prosthetic or orthotic system may issue a warning and/or take other corrective action.

In one embodiment a method for determining the position of a prosthetic or orthotic device in a moving object is provided. The method comprises detecting a stationary position of a user of a prosthetic or orthotic device. A first location of the prosthetic or orthotic device is identified with control circuitry operatively coupled to the prosthetic or orthotic device based on information received at a first time from a transmitting source located remotely to the prosthetic or orthotic device. A second location of the prosthetic or orthotic device is identified with the control circuitry based on information received at a second time from the transmitting source. A velocity of the prosthetic or orthotic device is calculated based on a distance between the first and second locations over a duration of time between the first time and the second time. The calculated velocity is compared to a threshold velocity. When the calculated velocity of the prosthetic or orthotic device exceeds the threshold velocity, a state of operation of the prosthetic or orthotic device is automatically adjusted, such as by initiating at least one of an automatic shut-off, a driving mode, or a relaxed mode of the prosthetic or orthotic device.

In another embodiment a method for actively adjusting a prosthetic or orthotic device is provided. The method comprises determining a location of the prosthetic or orthotic device user based on data wirelessly received from a transmitter remotely located to the prosthetic or orthotic device. The location is compared to environmental data stored in a memory. The environmental data is indicative of environmental variables corresponding to a plurality of known locations. At least one actuator actively adjusts movement of the prosthetic or orthotic device based at least in part on the comparison.

In another embodiment, a prosthetic or orthotic system is provided. The system comprises an actively-adjustable prosthetic or orthotic device having a global positioning system (GPS) receiver disposed on the prosthetic or orthotic device. The GPS receiver is configured to identify a location of the prosthetic or orthotic device. A processor is in communication with the GPS receiver. A memory is operatively coupled to the processor. The memory is configured to store environmental information corresponding to a plurality of predetermined locations. The processor is configured to identify the environmental information associated with at least one of the plurality of predetermined locations corresponding to the location of the prosthetic or orthotic device and to control movement of the prosthetic or orthotic device based at least in part on the identified environmental information.

In another embodiment, a prosthetic or orthotic system is provided. The system comprises a means for wirelessly receiving data from a remote transmitting device. The data is indicative of at least one of an absolute location of a prosthetic or orthotic device and the receiving means is coupled to or disposed on the prosthetic or orthotic device. The system also comprises a means for processing the data and instructing the prosthetic or orthotic device to initiate at least one of a power-off mode, a driving mode and a relaxed mode to restrict movement of the prosthetic or orthotic device based at least in part on the data.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to limit the invention. The following are brief descriptions of the drawings, which may not be drawn to scale.

In addition, methods and functions described herein are not limited to any particular sequence, and the blocks or states relating thereto can be performed in other sequences that are appropriate. For example, described blocks or states may be performed in an order other than that specifically disclosed, or multiple blocks or states may be combined in a single block or state.

DETAILED DESCRIPTION OF THE PREFERRED EMBODIMENTS

Some preferred embodiments of the invention described herein relate generally to prosthetic and orthotic systems. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The features of certain systems and methods will now be described with reference to the drawings summarized above. Throughout the drawings, reference numbers are re-used to indicate correspondence between referenced elements. The drawings, associated descriptions, and specific implementation are provided to illustrate embodiments of the invention and not to limit the scope of the invention.

The terms "prosthetic" and "prosthesis" as used herein are broad terms and are used in their ordinary sense and refer to, without limitation, any system, device or apparatus usable as an artificial substitute or support for a body part.

The term "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

The term "ankle device" as used herein is a broad term and is used in its ordinary sense and relates to any prosthetic, orthotic or ankle-assisting device.

The term "knee device" as used herein is a broad term and is used in its ordinary sense and relates to any prosthetic, orthotic or knee-assisting device.

Certain embodiments of the invention illustrate a prosthetic or orthotic device in communication with a remote transmitting source, platform, transceiver, transmitter or other like object, capable of facilitating identification of the global position and real-time movement of the device. In certain embodiments, the remote transmitting source can be one or more satellites. While certain embodiments are described herein with reference to utilizing global positioning system (GPS) technology, other types of wireless communication are included within the scope of the invention and can be used with the disclosed embodiments. For example, the remote transmitting source may include a radio frequency device, a satellite, a digital radio device, a BLUETOOTH device, a WI-FI device, and/or other applicable technology for wireless communication, such as mobile telephony networks or the like. Some examples of mobile telephony networks may include 3G, 4G, Edge, EVDO, GSM, CDMA, TDMA and the like.

Certain prosthetic or orthotic devices may have sensors, which provide limited micro-environmental information. For example, a prosthetic device may be able to recognize the acceleration of its own limb. But the typical device may be limited in providing information related to the macro-environmental context in which the prosthetic or orthotic device user is situated. For example, if the prosthetic device user is in a moving vehicle, such as a car, train, or plane, an accelerometer coupled to the prosthetic device may recognize the acceleration of the limb but not of the moving vehicle in which the prosthetic device user is located. While a certain prosthetic or orthotic devices may be able to operate without this information, this results in the user having less control and the danger that the prosthetic or orthotic user may make certain unsafe movements, such as the prosthetic limb activating when it should be in a relaxed mode.

Figure 1:
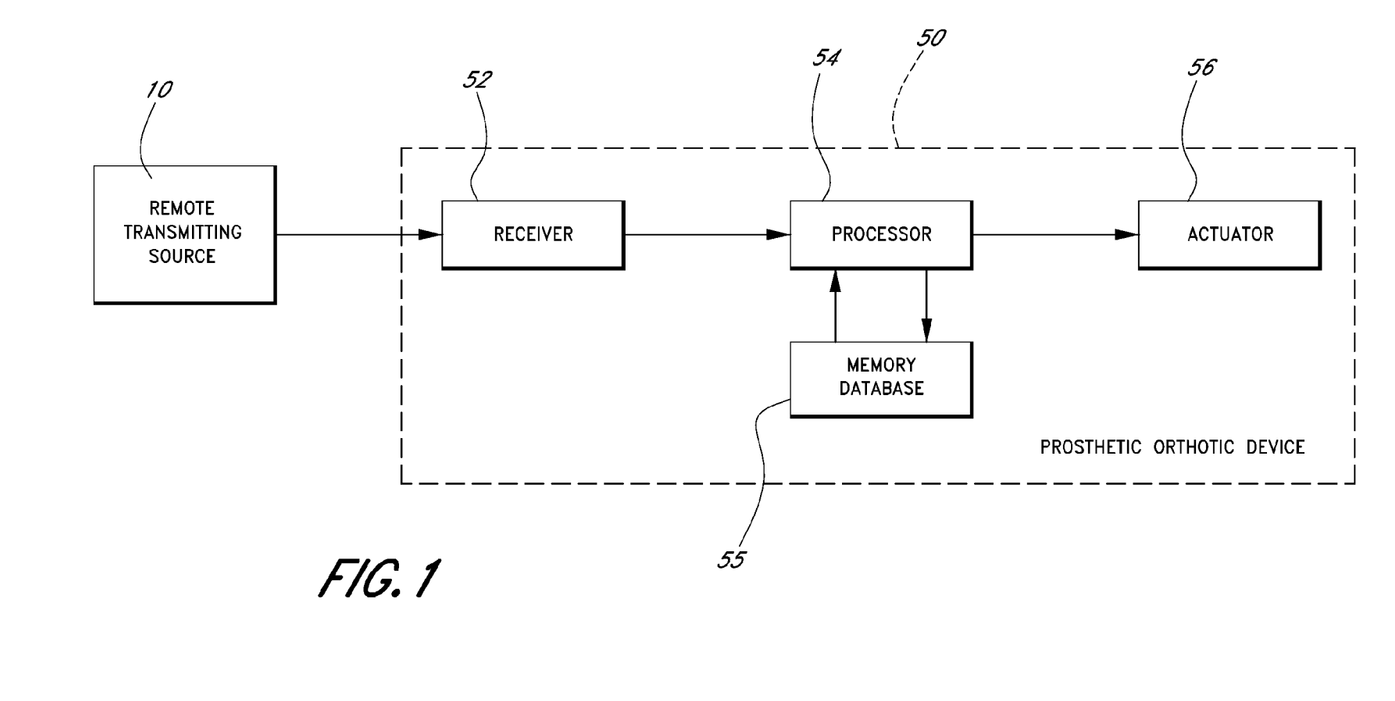
FIG. 1 illustrates a block diagram of a remote transmitting source in wireless communication with a prosthetic or orthotic device according to certain embodiments of the invention.

FIG. 1 illustrates a block diagram of a global positioning sensing system for a motion-controlled prosthetic or orthotic device according to certain embodiments of the invention. In general, a remote transmitting system and/or wireless communication system, such as a global positioning system, may be adapted for use in controlling movement of an actively-adjustable prosthetic or orthotic device, such as a knee device (or ankle device) for a transtibial or transfemoral user. In certain embodiments, the prosthetic or orthotic device includes one or more GPS sensors for detecting movement of the device and/or its user.

As illustrated, a remote transmitting source 10 wirelessly communicates data with a receiver 52 of a prosthetic or orthotic device 50. In certain embodiments, the data comprises position data and/or information usable to identify a location (e.g., longitude, latitude, elevation) of the prosthetic or orthotic device 50. In certain embodiments, the location comprises an absolute location, such as determined by longitudinal and latitudinal coordinates. In certain embodiments, the control circuitry of the prosthetic or orthotic device 50 then processes the data received by the receiver 52. In certain embodiments, the control circuitry may include the processor 54, the memory database 55, and/or the actuator 56.

In certain embodiments, the processor 54 analyzes the received data to determine a position, location, movement, speed and/or acceleration of the device 50. For instance, the processor 54 may identify a distance between a current location of the device 50 and a previous location of the device 50 and calculate a speed or velocity of movement of the device 50 over the period of time between the detection of the two locations. In yet other embodiments, the processor 54 compares the data to information stored in a memory database 55 (e.g., information corresponding to a plurality of predetermined locations). The processor 54 then instructs the actuator 56 to control movement (e.g., ankle rotation) of the device 50 based on the comparison, thereby providing intelligent control of the prosthetic or orthotic device 50.

In certain embodiments, the memory database 55 contains environmental data, such as terrain mapping information. The terrain mapping information may include known and stable terrain (e.g., metropolitan areas, city settings, streets, buildings, stairs or the like) and/or unknown and/or unstable terrain (e.g., rural areas, natural settings, beaches, mountainous terrain, or other areas having sand, gravel, or rocks or the like). For example, with regard to stable terrains, the memory database 55 may store information related to city boundaries, street maps, and street grading. Certain embodiments may contain building and stair locations and stair height. Upon receiving global positioning data that corresponds to stored, predetermined terrain mapping information in the memory database 55, the processor 54 can provide particular instructions based on the terrain map and/or can instruct the actuator 56 to shift to a high-power mode or a low-power mode, depending on the user's need for control, fineness of movements, and/or reaction speed.

For example, in one non-limiting embodiment, when a prosthetic device user visits a mountainous region, the receiver 52 in operative communication with the remote transmitting source 10 can detect the device user's location. In receiving the location information through the receiver 52, the processor 54 then compares the device's location to the terrain mapping information stored in the memory database 55. Upon detecting that the user is located in a mountainous region, the processor 54 may then instruct the actuator 56 of the prosthetic or orthotic device 50 to shift to a high-power mode to allow finer control over the uneven terrain.

In other embodiments, the memory database 55 contains environmental data, such as population density information. The population density information may include data indicative of high population areas and low populations areas. Similarly, upon receiving global positioning data that corresponds to stored population density information in the memory database 55, the processor 54 can instruct the actuator 56 to shift to a high-power mode for a higher population density location, such as for example greater than 10 million people, greater than 5 million people, or greater than 1 million people, in order to provide the prosthetic or orthotic device user with more control, finer motion, and/or a quicker reaction time.

The processor 54 may further instruct the actuator 56 to shift to a low-power mode for a lower population density location in order to prolong the battery life. Based on the disclosure, a skilled artisan would understand that various types of prosthetic and orthotic adjustment information can be correlated with particular location information to provide real-time feedback to the device according to embodiments of the invention.

In certain other embodiments, the receiver 52 in functional communication with the remote transmitting source 10, other microenvironment sensors (not shown), the processor 54, and the memory database 55, may also gather data related to the terrain mapping information and store it locally with reference to the global position of the user at the time the data was gathered. In certain other embodiments, the prosthetic or orthotic device has a transceiver (not shown) or a transmitter (not shown), which functions to transmit the gathered data to a remote global database or a server for processing and/or storage. In certain embodiments, the prosthetic or orthotic device reflects data from a remote transmitting source back to the remote transmitting source or another processing unit or server. A person skilled in the art would understand that different software and/or hardware configurations, parameters, and routines can be applied for each situation.

In certain embodiments, one or more GPS sensors may be adapted for use with a knee device (or ankle device) for a transtibial or transfemoral user. For example, embodiments of the invention can be practiced with a wide variety of active or passive prosthetic or orthotic limbs. For example, certain embodiments of the invention incorporate an active prosthetic knee and/or ankle. Embodiments of the invention can be practiced with a wider variety of prosthetic knees. These include, but are not limited to the POWER KNEE and the RHEO KNEE commercially available from Össur hf. (Iceland). Some embodiments of suitable prosthetic feet are disclosed in U.S. Pat. No. 6,610,101, issued on Aug. 26, 2003 and U.S. Pat. No. 7,314,490, issued on Jan. 1, 2008, the entirety of each of which is hereby incorporated by reference herein. Exemplary prosthetic feet can include FLEX-FOOT feet such as CETERUS, LP CETERUS®, VARI-FLEX, LP VARI-FLEX, TALUX, ELATION, and PROPRIO FOOT, each available from Össur hf. Some embodiments of suitable prosthetic feet and associated devices are also disclosed in U.S. Pat. No. 7,431,737, issued Oct. 7, 2008 and U.S. Patent Application Publication No. 2008/0215161, published Sep. 4, 2008, the entirety of each of which is hereby incorporated by reference herein.

Figure 2:
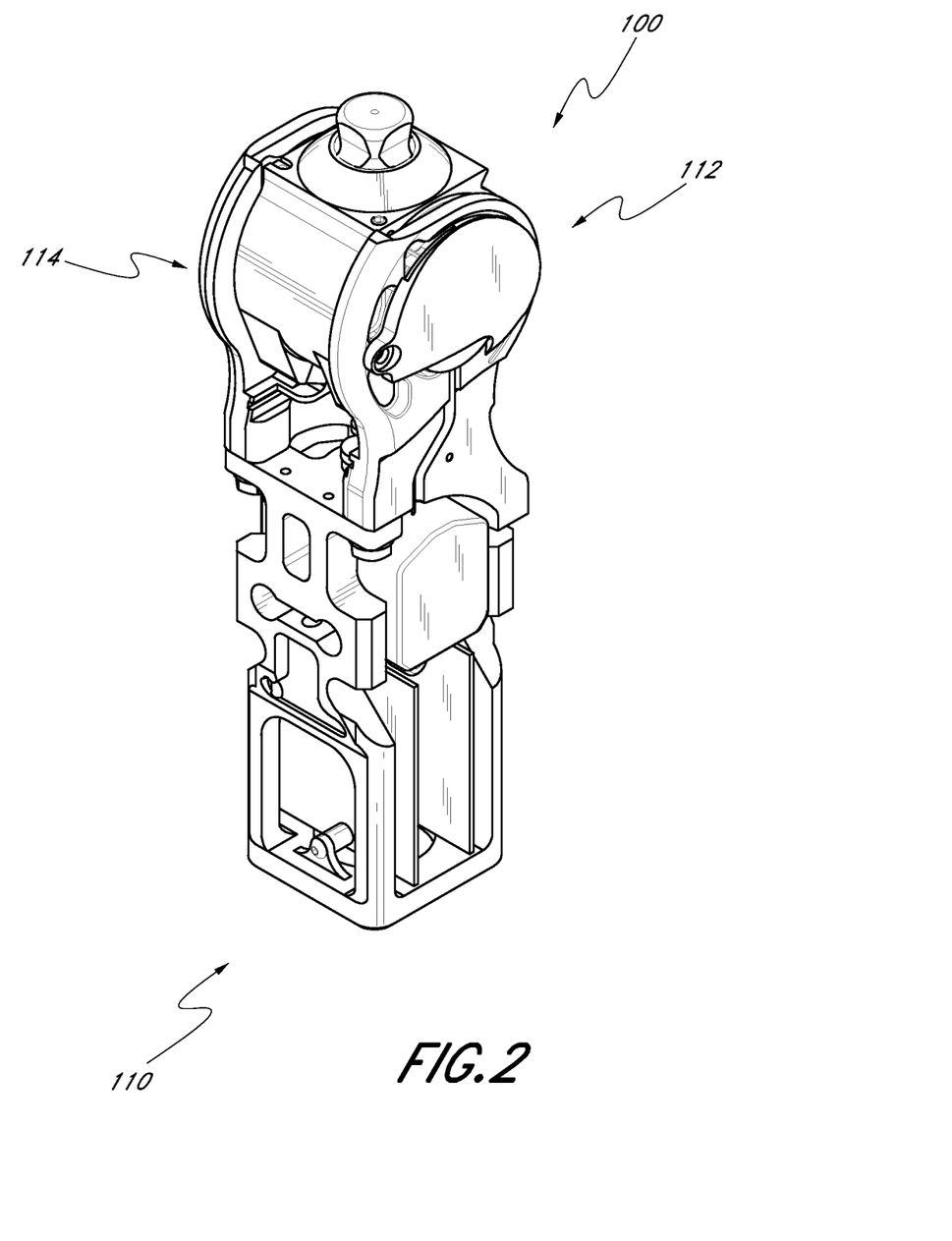
FIG. 2 illustrates a prosthetic knee device suitable for use with a global positioning system according to one embodiment.

FIG. 2 is an illustration of an embodiment of a lower limb prosthetic assembly that can be used in conjunction with a global positioning system, such as described above. The system or prosthesis 100 includes an electronically controlled active knee prosthetic assembly, system or prosthesis 110. In certain embodiments, the knee prosthesis 110 provides resistive forces to substantially simulate the position and motion of a natural knee joint during ambulation and/or other locomotory or stationary activities performed by an amputee. The prosthetic or artificial knee 110 is desirably safe, reliable and generally comfortable to use by the amputee.

The prosthetic knee 110 may comprise a variable-torque magnetorheological (MR) actuator assembly or braking system 112 and a processor 114 that can facilitate in monitoring and controlling the operation of the knee actuator 112. The prosthetic knee system 110 can provide resistive forces to substantially simulate the position and motion of a natural knee joint during ambulation and/or other locomotory activities performed by the amputee.

The prosthetic knee 110 can permit the amputee to move and/or adapt comfortably and safely in a wide variety of circumstances. For example, the prosthetic knee can aid in walking, running, sitting down, or when the device user encounters subtle or drastic changes in the terrain, topography and environment or ambient conditions, such as, when the device user lifts a suitcase or walks down a slope or encounters stairs, among others.

In certain embodiments of the invention, the prosthetic knee 110 may also comprise one or more GPS sensors (not shown). The global positioning sensor(s) (not shown) can function together with a remote transmitting source (not shown) to identify the global or relative position of the prosthetic knee device user. In some embodiments, the processor 114 uses this information to provide real-time feedback control to the actuator 112. For example, the processor 114 may use the global position information along with information related to stored terrain mapping information to increase or decrease the precise control of the device in relation to the environment. As another example, the processor 114 may use the global position information along with information related to the activity of the prosthetic knee 110 to initiate automatic shut off or a relaxed mode, as discussed more fully below.

Figure 3:
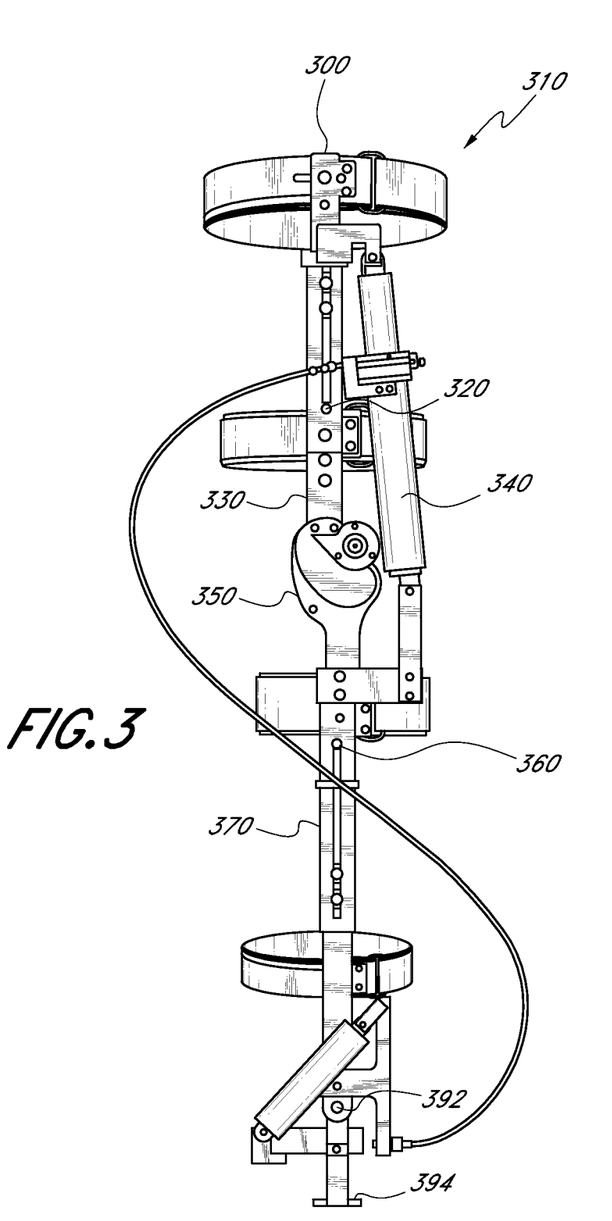
FIG. 3 illustrates an orthotic device suitable for use with a global positioning system according to one embodiment.

In certain embodiments, the global positioning system may be adapted for use with an orthotic device. As seen in FIG. 3, the orthotic device can be a Knee Ankle Foot device, which assists a patient suffering from muscular weakness or other problems affecting the patient's gait by providing support and compensation for diminished muscular function or weakness.

The orthotic device 310 shown in FIG. 3 comprises an orthotic frame 300 having an upper or proximal frame 330 and a lower or distal frame 370 joined by a mechanical knee joint 350. A foot support 394 can be joined to a distal end of the distal frame 370 by an ankle joint 392. The upper and lower frames 330, 370 can be adjustable in length, to accommodate fitting to patients of different sizes and physical needs.

In certain embodiments, a global positioning sensor 320 can be placed on the upper frame 330. In certain embodiments, a global positioning sensor 360 can be placed on the lower frame 370. The global positioning sensors 320, 360 may be operatively coupled to an actuator 340 and a processor (not shown) such that the global positioning data obtained by the sensors 320 and/or 360 provide feedback to the actuator and processor as to how much control to give the orthotic device user based on the environmental and terrain conditions.

Figure 4:
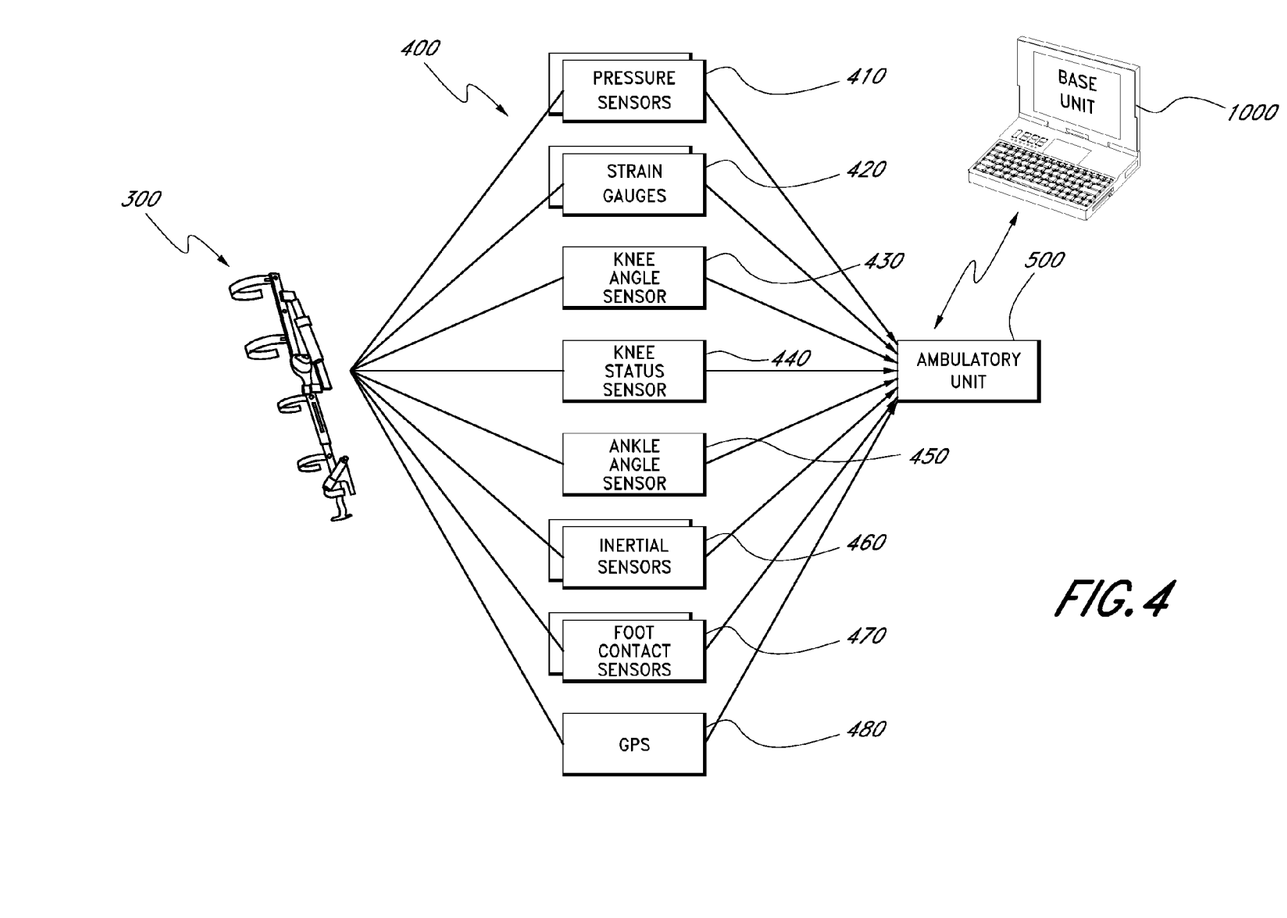
FIG. 4 illustrates a block diagram identifying instrumentation applied to an orthotic device according to one embodiment.

Referring to FIG. 4, the orthotic device can be instrumented with a multiple purpose sensor set 400, which enables measurement of physical variables related to comfort (pressure and strain), kinematics (sagittal plane angles of the knee and ankle joints, rotational velocities of the shank and foot segments, and foot accelerations, for example), global position, knee joint and actuator status, and other events related to ambulatory and related activities, including aspects of the gait cycle such as initial foot contact, foot flat, heel off, and toe off.

Data gathered from the sensor set 400 may be analyzed for biomechanical evaluation of the patient's use of the orthotic device, which may be useful for fitting of the orthotic device as well as monitoring the patient's progress and diagnosing problems with the patient relating to the orthotic device.

Further, real-time analysis of the data from the sensor set 400 allows identification of ambulatory and related activities that are performed by the patient, and can contribute to functional compensation provided by the orthotic device. For example, while in addition to control of the knee device, it can be recognized that a broader range of compensation strategies may be employed based on recognition of different activities such as sitting down, standing up, walking up or down stairs or a slope, or other activities that may place different requirements on the functionality of the orthotic device.

In one non-limiting example, the sensor set 400 allows for compensation strategies when the orthotic device user is walking up an incline. When the sensor set 400, which includes both micro-environmental sensors (e.g., knee and ankle angle sensors) and macro-environmental sensors (e.g., GPS sensors), detects that the user is about to walk up an incline, the ambulatory unit 500 may instruct the control system (such as the actuator) to increase to high-power mode, which would allow the device user to have greater control with less energy output.

The sensor set may include pressure sensors 410, strain gauges 420, a knee angle sensor 430, a knee status sensor 440, an ankle angle sensor 450, inertial measurement units (IMUs) 460, foot contact sensors 470, and a GPS sensor 480. An ambulatory data processing unit (ambulatory unit) 500 may be co-located with the orthosis (mounted to the orthotic frame 300 or carried by the patient, for example), to monitor the sensors and to process sensor data to control actuators of the orthotic device.

The ambulatory unit 500 may gather information from the various sensors disposed on the orthotic frame 300. The information, such as the global position data from sensor 480, may be processed locally by the ambulatory unit 500, and may be used to control actuators (such as the knee actuator 340) of the orthotic device in response to events or conditions that are detected or recognized by the ambulatory unit 500 based on analysis of the data, such as for example analysis of the global position data as compared to locally stored terrain mapping information. The ambulatory unit 500 also can provide an interface for forwarding gathered data to the base unit 1000 for further processing and analysis. In some embodiments, the base unit 1000 can also function as a remote transmitting center that stores terrain mapping data, receives and updates the terrain mapping database, and transmits real-time terrain mapping information to a device user.

In certain embodiments, the ambulatory unit 500 may also comprise a microprocessor connected to an area of main memory, comprising both read only memory (ROM), and random access memory (RAM). The microprocessor may be in communication with a storage device such as a disk storage device or a removable media memory device such as a removable memory card or the like. Input/output devices may be included to provide an interface to the sensors and actuators of the orthotic device 300. A control program may be stored in the ROM, or loaded into memory from the storage device, for execution by the microprocessor. The control program can function to read sensor data from the sensor inputs, and to evaluate the sensor data for control of actuators of the orthotic frame 300. The control program also may store the sensor data in the storage device for later recall and transmission to the base unit 1000, or transmit the sensor data to the base unit 1000 in real time.

In the electro-mechanical approach to changing the biasing force of the knee actuator 340, a control program executed by the ambulatory unit 500 determines when to signal the knee device to select the rigid setting or the flexible setting. While a simple control program may be employed to mimic the mechanical activation of the knee actuator 340, by simply measuring the angle of flexion of the ankle and unlocking the knee actuator 340 at a predetermined angle, a more advanced control program may provide a rule-based detection algorithm for the cycle-to-cycle selection of the knee actuator 340 setting based on a more comprehensive sampling of kinetic data of the orthotic frame 300.

A communication interface may be provided for communication between the ambulatory unit 500 and the base unit 1000. The communication interface may be a wireless interface, employing an RF, infra-red (IR), or other wireless communication medium. Alternatively, the communication interface may be wired, using a cable in connection with the base unit 1000

The global positioning system 480 may be disposed on the orthotic frame 300 and may provide information to the ambulatory unit 500 alone or in combination with the other sensors and gauges. In certain embodiments, the global positioning system 480 monitors the global position and real-time movement of the orthotic device 310 and sends the data to the ambulatory processing unit 500. The processing unit 500 then compares the data to a database of known environment situations. For example, if the orthotic device user is in a stationary position (e.g., a reclining position), but the global positioning system registers movement greater than a particular walking speed (e.g., a predetermined or dynamically calculated speed), the orthotic device may recognize that the device user is in a moving vehicle and restrict movement of the orthotic device, such as initiating automatic shut-off or another appropriate reaction (such as a relaxed mode, a driving mode or the like). While this example was given in terms of an orthotic device, the same functionality is applicable to a prosthetic device within the scope of the invention.

In certain embodiments, the threshold speed for the global positioning unit in conjunction with the seated position can be greater than 5 miles per hour (mph). In yet other embodiments, the threshold speed can be greater than 10 mph, greater than 20 mph, or greater than 50 mph. The automatic shut-off, relaxed mode, or driving mode may prevent the orthotic device from initiating movements that may be dangerous inside a moving vehicle, such as accidently pressing a pedal.

In some embodiments, where the driving mode is activated, the driving mode allows the device user's leg to remain in a relaxed state while the device user's ankle operates to control the foot pedals. For example, if the prosthetic or orthotic device user is in a car, the micro-environmental sensors would recognize that the user is in a stationary position (e.g., a seated position), but the global positioning unit would recognize a change in position and a speed above the threshold speed. The processor would then initiate automatic shut-off for the knee joint (or knee support in the case of an orthosis) but allow the ankle joint (or ankle support in the case of an orthosis) to function as normal. Alternatively, a relaxed mode may be used for a person in a passenger seat of a car or on a train. This would be similar to the previous example, but the processor would also initiate automatic shut-off for the ankle joint (or ankle support in the case of an orthosis).

In certain embodiments, if a device user has multiple orthotic devices, each orthotic device may initiate a different mode upon the device recognizing that the device user is in a moving vehicle. While these embodiments were described in terms of prosthetic and/or orthotic devices in relation to knees and/or ankles, a person of skill in the art would understand that other prosthetic and/or orthotic devices may be combined with a global positioning system and similar functions, such as, but not limited to, automatic shut-off and relaxed mode, may be used in response to environmental situations applicable to those specific prosthetic and/or orthotic devices.

Furthermore, an alert system may be used in conjunction with the global positioning system 480 on a prosthetic or orthotic device. For example, an alert system can provide an audible, tactile, or other signal or warning relating to a locked status of the knee actuator 340. The signal may be generated to indicate to the patient that the knee actuator 340 has been locked, so that the patient can confidently rely on the prosthetic or orthotic device to support her weight. Similarly, an alarm may be generated if a control signal has been sent to lock the knee actuator 340, but the locking mechanism is not properly activated. In other embodiments, the alert system can provide a signal to the device user when the prosthetic or orthotic device initiates a high-power or low power mode in response to the terrain mapping information.

Other types of sensors may be used in addition to, or in place of, those described. For example, microelectromechanical systems (MEMS) sensors, geomagnetic sensors, accelerometers, gyroscopes, or other types of sensors may be employed to provide movement or kinematic information that is unavailable from, or that is redundant to, other sensors.

Figure 5:
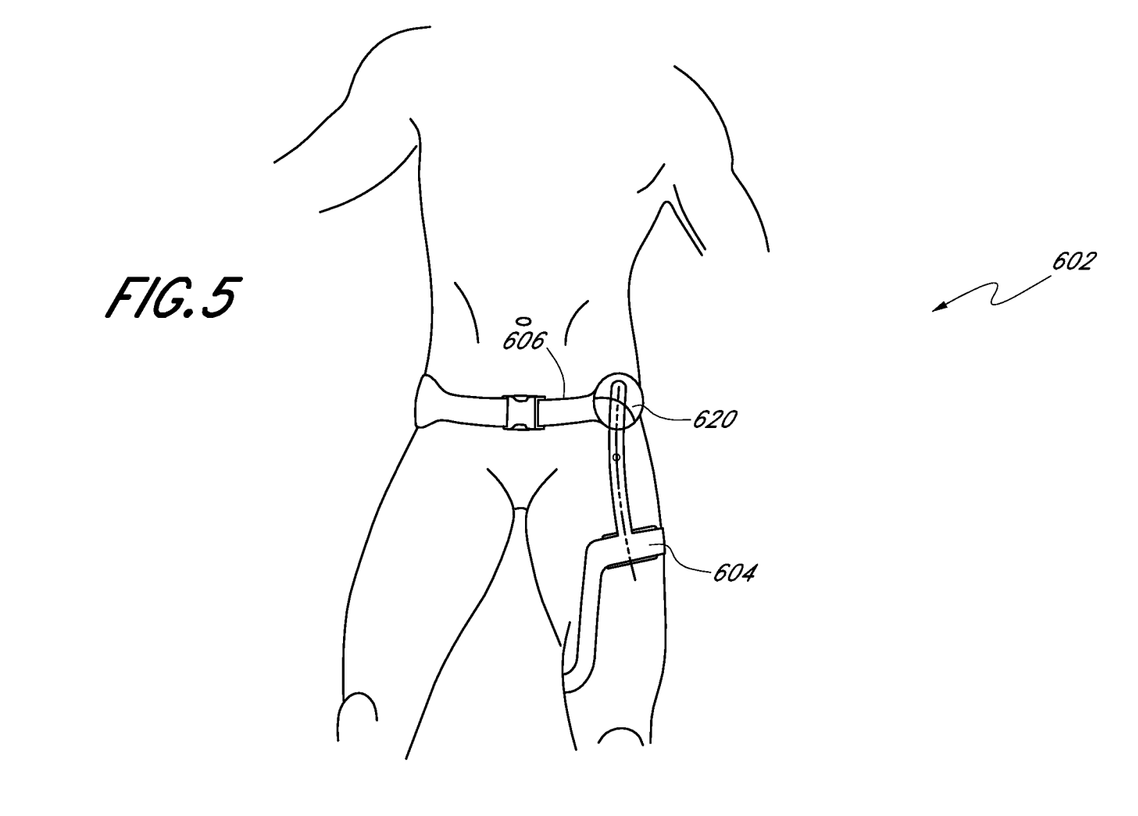
FIG. 5 illustrates another orthotic device suitable for use with a global positioning system according to one embodiment.

FIG. 5 shows an embodiment of a hip orthosis 602 for preventing the dislocation of a hip according to one embodiment of the invention. In FIG. 5, the hip orthosis 602 has been fitted to a person in standing position. The orthosis 602 can be provided with an upper leg engaging part 604, which can be arranged for engaging an upper leg of the person, in use, and a trunk engaging part 606, which can be arranged for engaging the trunk of the person, in use.

In certain embodiments, the hip orthosis 602 of FIG. 5 may also have a global positioning system 620 for monitoring sudden changes in direction, which may cause instability or injury to a device user with a weak hip. If the global positioning system senses that the device user is about to execute a U-turn, the processor coupled to the global positioning system may trigger the warning system to issue an alarm or vibration to alert the user to stop and use another movement. The global positioning system accomplishes this by sending sensory information related to the change in direction to the processor, which may then trigger the warning system to alert the prosthetic or orthotic device user of the potentially unsafe movement.

As discussed in U.S. Patent Publication Nos. 2009/0024062 and 2009/0024065, both filed on Jul. 18, 2008, each of which is hereby incorporated herein by reference in its entirety, in certain embodiments, the warning system having feedback characteristics may include sensors, a processor, and one or more feedback notification signals. The warning system may also have a locking mechanism such as an array of air cells insertable into the prosthetic or orthotic device, which inflate when triggered to constrict the limb and prevent unsafe movements. The feedback notification signals may include electric shocks or pulses, flashing lights or LEDs, auditory signals, and tactile signals. The auditory signals may include alarms, buzzers, beepers, whistles, or sirens. The tactile signals may include heat or vibration.

The warning system may include a combination of signals or a combination of signals and a locking mechanism. The warning system may be graduated and begin, for example, by triggering one or more feedback notification signals. If a device user chooses to ignore the signals, the warning system may then trigger the locking mechanism. The warning system may be categorized and trigger different feedback notification signals or the locking mechanism based on the assigned degree of danger of the predicted movement. A signal may last for less than 10 second, less than 5 seconds, or less than 1 second. In other embodiments, the signal can continue until manually turned off. The locking mechanism may last for less than 10 seconds, less than 5 seconds, or less than 1 second. In other embodiments, the locking mechanism may remain locked until manually released.

Moreover, certain control systems and modules described herein may comprise software, firmware, hardware, or any combination(s) of software, firmware, or hardware suitable for the purposes described herein. Software and other modules may be accessible via local memory, via a network, or via other means suitable for the purposes described herein. Data structures or indexes described herein may comprise computer files, variables, programming arrays, programming structures, or any electronic information storage schemes or methods, or any combinations thereof, suitable for the purposes described herein.

Certain embodiments of the invention are also described above with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flowchart and/or block diagram block or blocks.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flowchart and/or block diagram block or blocks. The computer program instructions may also be loaded onto a computer or other programmable data processing apparatus to cause a series of operations to be performed on the computer or other programmable apparatus to produce a computer implemented process such that the instructions which execute on the computer or other programmable apparatus provide means for implementing the acts specified in the flowchart and/or block diagram block or blocks.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for automatically adjusting a prosthetic or orthotic device, the method comprising:
   detecting a stationary position of a user of a prosthetic or orthotic device attached to the user;
   identifying with circuitry operatively coupled to the prosthetic or orthotic device a first geographic location identifying at least one of a longitude or latitude of the prosthetic or orthotic device based on information received at a first time from a transmitting source located remotely to the prosthetic or orthotic device;
   identifying with the circuitry a second geographic location identifying at least one of a longitude or latitude of the prosthetic or orthotic device based on information received at a second time from the transmitting source;
   calculating with circuitry a velocity of the prosthetic or orthotic device based on a distance between the first and second geographic locations over a duration of time between the first time and the second time while the user is in the stationary position;
   comparing with circuitry the calculated velocity to a threshold velocity; and
   when the calculated velocity of the prosthetic or orthotic device exceeds the threshold velocity while the user is in the stationary position, automatically adjusting with circuitry a state of operation of the prosthetic or orthotic device.

2. The method of claim 1, wherein the stationary position is a seated position.

3. The method of claim 2, wherein the threshold velocity is greater than 5 miles per hour.

4. The method of claim 3, wherein the threshold velocity is greater than 20 miles per hour.

5. The method of claim 1, wherein automatically adjusting a state of operation of the prosthetic or orthotic device comprises initiating at least one of an automatic shut-off, a driving mode, or a relaxed mode of the prosthetic or orthotic device.

6. The method of claim 5, wherein initiating the driving mode comprises automatically restricting movement by a knee joint of the prosthetic or orthotic device.

7. The method of claim 5, wherein initiating the relaxed mode comprises automatically restricting movement of both a knee joint and an ankle joint of the prosthetic or orthotic device.

8. The method of claim 1, wherein said identifying the first and second geographic locations with the circuitry comprises detecting the first and second geographic locations with at least one global positioning system (GPS) sensor.

9. The method of claim 1, wherein identifying the first geographic location comprises identifying an elevation of the prosthetic or orthotic device.

10. A method for actively adjusting a lower limb prosthetic or orthotic device, the method comprising: determining a global location of the prosthetic or orthotic device user based on data wirelessly received from a transmitter remotely located to the prosthetic or orthotic device; comparing the determined global location to environmental data related to the determined global location that was previously stored in a memory prior to the device reaching said determined global location, wherein said environmental data is indicative of environmental variables corresponding to a plurality of known global locations and comprises population density information; and actively adjusting with at least one actuator movement of the prosthetic or orthotic device based at least in part on said comparison.

11. The method of claim 10, wherein the environmental data further comprises terrain information.

12. The method of claim 11, wherein the terrain information comprises stable and unstable terrain mapping information.

13. The method of claim 10, wherein said determining comprises wirelessly receiving the data via at least one sensor operatively coupled to the prosthetic or orthotic device.

14. The method of claim 13, wherein the at least one sensor comprises a global positioning system (GPS) receiver.

15. The method of claim 13, wherein the at least one sensor comprises a radio frequency (RF) sensor.

* * * * *